(12) United States Patent
Kota

(10) Patent No.: US 12,270,579 B2
(45) Date of Patent: Apr. 8, 2025

(54) FLEXIBLE THERMOELECTRIC DEVICE

(71) Applicant: Kiran Kota, Oceanside, CA (US)

(72) Inventor: Kiran Kota, Oceanside, CA (US)

( * ) Notice: Subject to any disclaimer, the term of this patent is extended or adjusted under 35 U.S.C. 154(b) by 0 days.

(21) Appl. No.: 18/010,872

(22) PCT Filed: Jul. 15, 2022

(86) PCT No.: PCT/US2022/037289
§ 371 (c)(1),
(2) Date: Dec. 16, 2022

(87) PCT Pub. No.: WO2023/003772
PCT Pub. Date: Jan. 26, 2023

(65) Prior Publication Data
US 2024/0167736 A1    May 23, 2024

Related U.S. Application Data

(60) Provisional application No. 63/224,525, filed on Jul. 22, 2021.

(51) Int. Cl.
*F25B 21/02* (2006.01)
*F28C 3/00* (2006.01)

(52) U.S. Cl.
CPC .............. *F25B 21/02* (2013.01); *F28C 3/005* (2013.01)

(58) Field of Classification Search
None
See application file for complete search history.

(56) References Cited

U.S. PATENT DOCUMENTS

| | | | | |
|---|---|---|---|---|
| 2,991,627 A | * | 7/1961 | Suits | A61F 7/10 62/3.5 |
| 3,648,469 A | * | 3/1972 | Chapman | H10N 10/00 5/636 |
| 4,470,263 A | * | 9/1984 | Lehovec | A42C 5/04 62/3.5 |
| 4,846,176 A | * | 7/1989 | Golden | A61F 7/02 607/104 |
| 4,860,748 A | * | 8/1989 | Chiurco | A61F 7/007 607/96 |

(Continued)

FOREIGN PATENT DOCUMENTS

| | | | | |
|---|---|---|---|---|
| BR | 9005228 A | * | 9/1991 | A47C 7/744 |
| CN | 108370615 A | * | 8/2018 | B60N 2/56 |

(Continued)

*Primary Examiner* — Jenna M Maroney
(74) *Attorney, Agent, or Firm* — CP LAW GROUP PC; Cy Bates

(57) ABSTRACT

A flexible thermoelectric device includes a plurality of modules wherein each module includes a thermoelectric component disposed between a thermally conductive plate and a heat sink. Each thermally conductive plate is in contact with at least one spacer, which is disposed on the same side of the plate as the thermoelectric component and heat sink, such that the spacers together form a clearance between external bodies and the heat sinks. An elastic material is coupled to the plurality of modules, the plurality of spacers, or a combination thereof. The device can conform to and cool a large surface area of a user's body, while reducing strain on fragile components.

17 Claims, 13 Drawing Sheets

(56) References Cited

U.S. PATENT DOCUMENTS

| | | | | |
|---|---|---|---|---|
| 4,962,761 A * | 10/1990 | Golden | A61F 7/02 | 607/104 |
| 4,969,684 A * | 11/1990 | Zarotti | A47C 27/082 | 297/284.3 |
| 5,097,829 A * | 3/1992 | Quisenberry | A61F 7/02 | 219/490 |
| 5,174,266 A * | 12/1992 | Evdokimo | F02M 31/20 | 123/557 |
| 5,653,741 A * | 8/1997 | Grant | A61F 7/007 | 607/114 |
| 5,800,490 A * | 9/1998 | Patz | A61F 7/007 | 607/108 |
| 5,899,077 A * | 5/1999 | Wright | H10N 10/00 | 62/3.7 |
| 6,084,209 A * | 7/2000 | Reusche | H05B 3/342 | 219/217 |
| 6,823,678 B1 * | 11/2004 | Li | F25B 21/04 | 62/3.5 |
| 7,022,093 B2 * | 4/2006 | Smith | A61F 7/02 | 602/14 |
| 8,388,056 B2 * | 3/2013 | Smith | A47C 4/286 | 297/16.2 |
| 9,078,478 B2 * | 7/2015 | Ross, Jr. | A61B 5/6804 | |
| 9,267,714 B2 * | 2/2016 | Hou | H10N 10/13 | |
| 9,310,112 B2 * | 4/2016 | Bell | B60H 1/00271 | |
| 9,375,345 B2 * | 6/2016 | Levinson | A61F 7/0085 | |
| 9,408,744 B2 * | 8/2016 | Allen | A61F 7/02 | |
| 9,421,123 B2 * | 8/2016 | Lee | A61N 1/36021 | |
| 9,907,692 B2 * | 3/2018 | Binversie | A61N 1/0456 | |
| 9,962,284 B2 * | 5/2018 | Robinson | A61F 7/02 | |
| 11,395,760 B2 * | 7/2022 | Levinson | A61F 7/02 | |
| 11,419,753 B2 * | 8/2022 | Vergara | F25B 21/02 | |
| 11,419,754 B2 * | 8/2022 | Vergara | A61F 7/0053 | |
| 11,857,004 B2 * | 1/2024 | Cauchy | H10N 10/13 | |
| 11,903,872 B2 * | 2/2024 | Vergara | F28F 3/08 | |
| 2002/0026226 A1 * | 2/2002 | Ein | A61F 7/007 | 606/112 |
| 2002/0164473 A1 * | 11/2002 | Buckley | C08K 5/0008 | 2/93 |
| 2003/0102296 A1 * | 6/2003 | Nelson | H05B 3/342 | 219/217 |
| 2004/0159109 A1 * | 8/2004 | Harvie | A41D 13/0051 | 62/3.5 |
| 2005/0065581 A1 * | 3/2005 | Fletcher | F28F 3/12 | 607/104 |
| 2005/0143797 A1 * | 6/2005 | Parish | A61F 5/34 | 607/104 |
| 2008/0077201 A1 * | 3/2008 | Levinson | G05D 23/22 | 600/549 |
| 2008/0097562 A1 * | 4/2008 | Tan | A61M 5/44 | 607/113 |
| 2008/0188915 A1 * | 8/2008 | Mills | A61F 7/007 | 607/112 |
| 2008/0249524 A1 * | 10/2008 | Dunning | A61B 18/16 | 606/41 |
| 2008/0287839 A1 * | 11/2008 | Rosen | A61H 9/005 | 601/18 |
| 2009/0000309 A1 * | 1/2009 | Hershberger | H10N 10/13 | 62/3.5 |
| 2009/0264969 A1 * | 10/2009 | Gammons | A61F 7/02 | 607/104 |
| 2009/0312822 A1 * | 12/2009 | Besner | A61N 5/06 | 607/100 |
| 2010/0198322 A1 * | 8/2010 | Joseph | A61F 7/007 | 607/108 |
| 2010/0280581 A1 * | 11/2010 | Cushman | A61F 7/03 | 607/112 |
| 2011/0030754 A1 * | 2/2011 | Smythe | H10N 10/17 | 29/623.2 |
| 2011/0071603 A1 * | 3/2011 | Moore | A61F 7/007 | 607/96 |
| 2011/0227389 A1 * | 9/2011 | Gomes | B60N 2/5635 | 297/452.43 |
| 2012/0239123 A1 * | 9/2012 | Weber | A61F 7/10 | 607/104 |
| 2014/0222121 A1 * | 8/2014 | Spence | A61F 7/02 | 607/104 |
| 2014/0276257 A1 * | 9/2014 | Santa Maria | A61H 9/005 | 601/18 |
| 2014/0352325 A1 * | 12/2014 | Brown | F25B 21/04 | 62/3.2 |
| 2015/0182375 A1 * | 7/2015 | Binversie | A61F 7/007 | 601/18 |
| 2015/0238349 A1 * | 8/2015 | Giuliani | A61F 7/00 | 602/2 |
| 2015/0366703 A1 * | 12/2015 | Du | A61F 7/02 | 607/104 |
| 2016/0035957 A1 * | 2/2016 | Casey | H10N 10/13 | 136/230 |
| 2016/0178251 A1 * | 6/2016 | Johnson | A61F 7/02 | 62/3.5 |
| 2016/0270952 A1 * | 9/2016 | Vergara | A61F 7/02 | |
| 2017/0027053 A1 * | 1/2017 | Moczygemba | H05K 1/0203 | |
| 2017/0354190 A1 * | 12/2017 | Cauchy | B60N 2/5635 | |
| 2018/0098903 A1 * | 4/2018 | Vergara | A61F 7/0085 | |
| 2018/0110266 A1 * | 4/2018 | Lee | A61B 5/6804 | |
| 2019/0099287 A1 * | 4/2019 | Vergara | A61F 7/0085 | |
| 2019/0099288 A1 * | 4/2019 | Vergara | A61F 7/007 | |
| 2019/0262169 A1 * | 8/2019 | Vergara | A61F 7/0053 | |
| 2020/0025424 A1 * | 1/2020 | Cauchy | B60N 2/5657 | |

FOREIGN PATENT DOCUMENTS

| | | | | |
|---|---|---|---|---|
| CN | 108886085 A * | 11/2018 | | B60N 2/5678 |
| DE | 4238291 A1 * | 5/1994 | | A61F 7/10 |
| DE | 102009038311 A1 * | 2/2011 | | B60N 2/5635 |
| DE | 202018103008 U1 * | 8/2018 | | A47C 7/744 |
| WO | WO-2005047056 A1 * | 5/2005 | | B60N 2/5635 |
| WO | WO-2016160691 A1 * | 10/2016 | | A61F 7/0053 |

* cited by examiner

Thermosiphon mechanism

Pump-reservoir mechanism

FLEXIBLE THERMOELECTRIC DEVICE

TECHNICAL FIELD

This invention relates to a thermoelectric device; more particularly a flexible thermoelectric device used for cooling and/or heating.

BACKGROUND ART

For millennia, humans have been experimenting with ways to stay cool: from ancient adobe buildings that used thermal mass to stabilize temperatures to skyscraper-sized air conditioning systems.

Insulation and air cooling have by far been the most popular duo. Since its initial commercialization, the vapor compression cycle quickly became and has remained the primary method of removing unwanted heat. It is primarily used to cool down air to comfortable levels for humans and animals (air conditioning) or to useful/safe temperatures for foods, beverages, chemicals, etc. (refrigeration). This method of using air as an intermediary for cooling is popular due to its convenience: no need for direct contact to a cold object means that the people and objects that need to be cooled can move quickly and freely. Evaporative cooling (e.g. swamp coolers) is another common method of air cooling in drier parts of the world.

Where insulation and air cooling are not feasible, direct cooling methods are used. Direct cooling could be grouped into three categories: body of water (jumping in a pool or drinking a jug of ice water), evaporative garments (a wet towel around the neck or an evaporative cooling vest), and thermoelectric devices (Peltier neck or back coolers).

Thermoelectric components are not commonly used for large personal cooling loads or amorphous bodies due to their rigidity. Two solutions that have been put forth in prior art to address this problem are a) thermoelectrically cooling water and then pumping the water through tubing embedded in furniture surfaces (hereafter "cooled tube design") and b) using flexible substrates instead of rigid, commonly ceramic ones (hereafter "flexible substrate design").

SUMMARY OF INVENTION

Technical Problem

The reasons existing solutions are inadequate or inefficient for the future are threefold: a) The move to sedentary work and digital entertainment make residential and commercial air cooling inefficient where direct-cooling stationary devices could be used. However, existing direct-cooling solutions are inconvenient, inefficient, or weak; b) Global warming increases the demand for cooling solutions, while air conditioning typically contributes to greenhouse gas emissions; c) Many people in developing countries can't afford air conditioning, which could prove increasingly fatal and heighten conflicts in a warming world.

Direct cooling is preferred for stationary work and entertainment, but existing solutions are inconvenient and inefficient. Sometimes the reasons are obvious: one can't jump in a pool in the middle of their work day or off time without taking time to dry off and dress back up. Evaporative garments add humidity and the vaguely annoying feeling of "stickiness". Existing thermoelectric devices are small and inefficient because they use one- or two-component designs with air-cooled heat sinks. Liquid-cooled thermoelectric personal devices are not commonly available due to their assumed weight and large, rigid (i.e. uncomfortable) structure.

Existing flexible thermoelectric devices have some drawbacks. The cooled tube design is electrically inefficient because it pumps heat against the temperature gradient. Commercially available devices with a cooled tube design use air cooling for the hot side of the component(s), which is also electrically inefficient. The flexible substrate design has not been significantly adopted commercially. It is assumed that the manufacturing process for such devices is more expensive, as it requires additional measures to be taken to maintain the durability of electrical connections between semiconductors. Furthermore, cooling the hot side of a flexible substrate necessitates the use of a flexible heat sink, which may either add additional costs compared to common metal heat sinks or limit the potential applications.

Air-conditioning is self-perpetuating when it comes to global warming. Even assuming 100% renewable power for air conditioning and the most efficient solar PV generation, converting incoming sunlight into hot air may have a warming effect when compared to letting that sunlight partially reflect off the ground back into space.

The lack of energy infrastructure and prohibitive cost of air conditioning in developing countries means many people in those regions run hot all the time. Research has been conducted comparing heat exposure to interpersonal conflict. For example, violent crime rates increase in the summer. Knowing that, it isn't far-fetched to assume that a warmer world will be a more violent one if there isn't an efficient way to relieve that heat stress.

Solution to Problem

An efficiently cooled thermoelectric device that can cover a large surface area of the user's body is disclosed. For such a device to be adopted, it should be comfortable and cause minimal interference with the user's regular activities. The invention in the instant disclosure allows for efficient cooling in a form factor that is comfortable, durable, and easy to use.

The efficiency of existing thermoelectric components (e.g. Peltier modules) is based primarily on a combination of a) difference between the temperature of the substrate coupled to the heat load (TL) and that of the substrate coupled to the heat sink (Ts) (coefficient of performance improves as TL-Ts increases) and b) the ratio of the current passing through the device to the level of current that maximizes heat transfer (I/Imax; lower is generally more efficient but reduces cooling capacity).

To maximize TL-Ts, the cold side of the thermoelectric component must be as closely coupled to the heat load as possible. This means a large surface area of thermally conductive material (e.g. copper or aluminum plates) coupled to the cold side of the component, with one face exposed for close contact to the user's body. Additionally, the hot side of the component must be as closely coupled to a thermally conductive heat sink as possible. This is best done with metal fluid-cooling blocks or fluid coolant directly passing over or within the component substrate. Minimizing I/Imax is easier: utilize thermoelectric components that meet predetermined specifications and then limit the current supplied to them using a fixed/predictable voltage or current power source.

Targeting the back or rear thigh (hamstring) area, where humans tend to store less fat and have a larger volume of blood flow, is advantageous. To make such a large surface area of rigid material comfortable to rest against for an amorphous area of the body, it should be separated into sections with flexible couplings interconnecting those sections. Each section should have its own thermoelectric component. Each component should have its own heat sink or be coupled to a flexible heat sink. When compared to the flexible substrate design, it could be said that the invention in the instant disclosure uses "inter-component" rather than "intra-component" flexibility.

With so many fragile components moving in different directions and subject to mechanical stresses, the components and methods of coupling (e.g. adhesives) must be protected. The invention uses a combination of spacers, elastic material, and/or coverings to create shielding from external bodies.

Advantageous Effects of Invention

The invention allows for powerful cooling at a relatively low DC wattage. This has a few resulting advantages: lower energy costs for the user; an embodiment can easily be powered by a portable battery bank, solar panel, or a 12V outlet in a vehicle; the system produces less waste heat.

The invention does not require external refrigeration devices or preparatory time. It is able to operate on-demand using a room temperature fluid. This means less interference with the user's regular activities, allowing the invention to compete more effectively with other passive systems. This is also advantageous when compared to air cooling systems that need time to circulate a large volume of air in order to reduce the average temperature to the target temperature.

The invention does not produce excess humidity, which is advantageous compared to popular cooling methods other than air conditioning.

The invention is relatively inexpensive compared to air cooling systems even before accounting for insulation, duct work, and high wattage infrastructure.

The invention uses fewer moving parts than air cooling, making it quieter and less susceptible to long-term wear and tear.

The invention is lightweight and durable and takes up a relatively small amount of space, allowing for portability and reducing real estate overhead (e.g. square footage costs).

In some embodiments, the polarity of the thermoelectric components can be reversed. This allows for heating and re-use of waste heat. In embodiments that utilize a reservoir, this reverse setting can be used to pre-chill the fluid.

In some geographies and automobile categories, the invention can be used to replace air conditioning altogether, reducing complexity in the engine bay and improving fuel performance.

BRIEF DESCRIPTION OF THE DRAWINGS

Other features, combinations, and embodiments will be appreciated by one having the ordinary level of skill in the art of thermoelectric devices upon a thorough review of the following details and descriptions, particularly when reviewed in conjunction with the drawings, wherein.

DETAILED DESCRIPTION

Figure 1A:
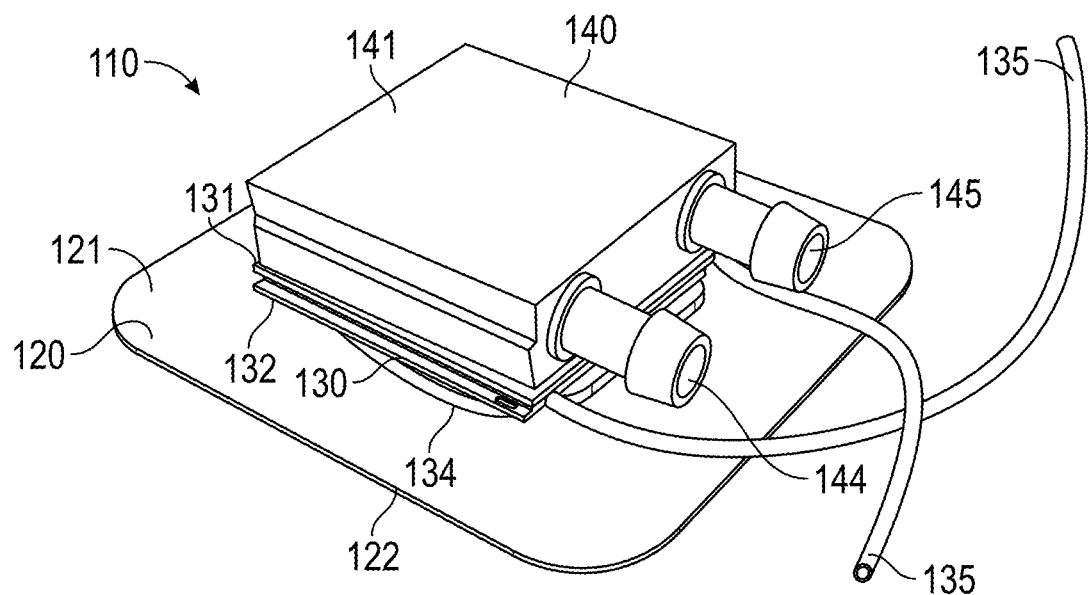
FIG. 1A shows a perspective view of one of a plurality of modules in accordance with a first illustrated embodiment.

For purposes of explanation and not limitation, details and descriptions of certain preferred embodiments are hereinafter provided such that one having ordinary skill in the art may be enabled to make and use the invention. These details and descriptions are representative only of certain preferred embodiments, however, a myriad of other embodiments which will not be expressly described will be readily understood by one having skill in the art upon a thorough review of the instant disclosure. Accordingly, any reviewer of the instant disclosure should interpret the scope of the invention only by the claims, as such scope is not intended to be limited by the embodiments described and illustrated herein.

The term "elastic material" means an amorphous solid material or combination of materials that can bend, compress, or elongate without inelastic deformation, and not necessarily having a tendency to return to any shape, with the following minimum specifications: Bending—1 mm thickness material can bend from its original shape at least 1° per 10 mm length; Compression or elongation—at least 1% change from original length The term "thermoelectric component" means a component that exhibits the thermoelectric effect of converting a temperature gradient to electricity or vice versa.

The term "heat sink" means a device or substance for absorbing excessive or unwanted heat.

The term "spacer" means a liquid or solid material, or a gas that cannot be completely displaced due to sealing, hydraulic pressure, or magnetic force The term "fluid" means a gas or liquid The term "continuous body" means a body with a plurality of contained bodies, wherein each of the contained bodies is coupled to at least one of the other contained bodies The term "smooth surface" means a surface or plurality of surfaces adjacent to each other that has no lumps or dips greater than 1.5 mm in height or depth, respectively.

The term "clearance" means an empty space or gap between two surfaces.

The term "periphery" means the outer edge or limits of an object.

The term "reservoir" means a container configured increase the amount of fluid in a fluidly coupled system Unless explicitly defined herein, terms are to be construed in accordance with the plain and ordinary meaning as would be appreciated by one having skill in the art.

GENERAL DESCRIPTION OF EMBODIMENTS

In one embodiment, a flexible thermoelectric device is disclosed. The thermoelectric device comprises a plurality of modules. Each of the plurality of modules comprises a thermally conductive plate having a plate top surface and a plate bottom surface opposite the plate top surface, a thermoelectric component having a component top side and an component bottom side opposite the component top side, and a heat sink having a heat sink top surface, a heat sink bottom surface opposite the heat sink top surface, and a hollow cavity disposed therebetween. The component bottom side is coupled to the plate top surface, and the heat sink bottom surface is coupled to the component top surface. The device further comprises a plurality of spacers wherein at least one of the plurality of spacers is disposed on each of the plurality of plate top surfaces. Each of the plurality of spacers comprises a spacer top surface wherein each of the spacer top surfaces extends vertically above the heat sink top surface thereby forming a clearance therebetween. An elastic material is coupled to the plurality of modules, the plurality of spacers, or a combination thereof, thereby forming a continuous body. One or more power sources are electrically coupled to the plurality of modules for powering the thermoelectric components.

In some embodiments, the flexible thermoelectric device may further comprise a device outer periphery surrounding each of the plurality of modules wherein at least one of the plurality of spacers is disposed between each of the plurality of modules and the device outer periphery. In some embodiments, the device outer periphery is an outer edge of the elastic material.

In some embodiments, at least one of the plurality of spacers may be disposed between neighboring modules.

In some embodiments, the heat sink of each of the plurality of modules may be configured to be fluidly coupled to at least one other heat sink.

In some embodiments, the heat sink may further comprise a first aperture, a second aperture, a first fluid tube coupled to the first aperture, and a second fluid tube coupled to the second aperture. The first and second fluid tubes and the elastic material may be independent and distinct. The first fluid tube and the second fluid tube may each extend through at least one of the plurality of spacers.

In some embodiments, the plurality of modules may be fluidly coupled in series, parallel, or a combination thereof.

In some embodiments, the flexible thermoelectric device may further comprise a reservoir fluidly coupled to the plurality of modules. In some embodiments, the flexible thermoelectric device may further comprise a pump fluidly coupled to the reservoir.

In some embodiments, the plate top surface may extend beyond the component bottom surface.

In some embodiments, the elastic material may surround an entire perimeter of the thermoelectric component. In some embodiments, at least one of the plurality of spacers may surround each of the thermoelectric components of each of the plurality of modules.

In some embodiments, the plurality of spacers may surround each of the heat sinks of each of the plurality of modules.

In some embodiments, the flexible thermoelectric device may further comprise a removable front cover disposed over each plate bottom surface of the plurality of modules.

In some embodiments, the plate bottom surface of each of the plurality of modules may form a bottom device plane, the bottom device plane further comprising a membrane disposed on the bottom device plane. The membrane may comprise a membrane bottom surface and a membrane top surface opposite the membrane bottom surface, wherein the membrane bottom surface and the plate bottom surface of each of the plurality of modules may form a smooth surface.

In some embodiments, the elastic material may comprise the membrane.

In some embodiments the membrane may comprise a non-absorbing material.

In some embodiments, the flexible thermoelectric device may further comprise a non-absorbing layer coupled to the membrane top surface.

In some embodiments, the membrane bottom surface may comprise a contact surface of a piece of furniture. In some embodiments, the membrane bottom surface may comprise a contact surface of a seat in a vehicle.

In some embodiments, the elastic material may be coupled to the plate of each of the plurality of modules.

In some embodiments, the flexible thermoelectric device may further comprise a relay switch electrically coupled to one or more of the thermoelectric components, wherein a sensor is electrically coupled to the relay switch.

In some embodiments, the heatsink may be configured to comprise an amount of fluid in the hollow cavity, the heat sink being configured to heat or cool the thermoelectric component by conduction through the heat sink bottom surface.

In some embodiments, the heatsink may be configured to comprise an amount of fluid in the hollow cavity, the heat sink being configured to directly cool or heat the component top surface via one or more openings in the heat sink bottom surface.

In another embodiment, a flexible thermoelectric device is disclosed. The flexible thermoelectric device comprises a plurality of thermoelectric components. Each of the plurality of thermoelectric components comprises a component top side, a semiconductor material, and component bottom side, wherein the semiconductor material is disposed between the component top side and the component bottom side. The device further comprises an elastic material comprising an elastic mesh having an elastic top surface, an elastic bottom surface, and a hollow cavity disposed therebetween. The elastic bottom surface is coupled to the plurality of thermoelectric components, thereby forming a continuous body. One or more power sources are electrically coupled to the plurality of thermoelectric components.

In some embodiments, the elastic mesh may be configured to comprise an amount of fluid in the hollow cavity, the elastic mesh being configured to directly cool or heat the top substrates via one or more openings in the elastic bottom surface.

In some embodiments, a vapor barrier may be disposed between the elastic bottom surface and the plurality of thermoelectric components.

In some embodiments, a plurality of thermally conductive plates may be coupled with the plurality of component bottom sides.

Manufacturing

As an example, one embodiment of the flexible thermoelectric is described below. One having skill in the art will appreciate there is a myriad of parts and designs for accomplishing the device.

Parts list may comprise: some multiple of four thermally conductive plates, an equal number of thermoelectric components, an equal number of heat sinks, ⅛ inch or less project foam sheet, ¾ inch EVA foam, vinyl tubing, reservoir, 12V submersible water pump, 12V power source, marine-grade fabric Thermally conductive plates can be made of aluminum or copper sheet and should be as thin as possible (to reduce thermal resistance between the user's body and the thermoelectric component) while still being thick enough to provide durability. Plates may bend upon dropping in addition to normal use, such as the device being used as a back rest. 0.025-inch thickness plates have been shown to work well. The length and width of the plates should be large enough to cover the thermoelectric components, and additionally large enough to accommodate the coupling of spacers. Furthermore, corner rounding the plates improves comfort while reducing the amount of area available for spacer couplings. The most inexpensive commercially available thermoelectric components (Peltier modules) tend to be 40 mm by 40 mm. 3 inch by 3 inch plates are large enough to cover that area, while allowing room for spacers and ½ inch radius corner rounding.

The binding surface (top) of the plates can be scored to improve adhesion with other components. The Peltier modules can be centered on the plates for stability and to optimize heat spreading (improving electrical efficiency). A thermally conductive epoxy or glue is best for coupling the Peltier module to the plate.

A heat sink, commercially available as an "aluminum water cooling block", can be adhered, again with thermally conductive adhesive, to the top surface of the Peltier module. The heat sink should be large enough to cover the entire substrate in order to maximize heat transfer. If they are too large, they will add weight and reduce the binding area on the plate for spacers, but this would also improve heat transfer and efficiency.

Spacers can be made with a dense foam. For example, ¾ inch EVA foam marketed for sound dampening can be used. Prior to adhering these to the plates, it is recommended to bind a thin layer (⅛ inch or less) of foam, with cutouts for the Peltier modules, that covers multiple plates. This can provide the flexible, elastic material between plates/modules while also creating a binding surface on the bottom layer for a membrane, discussed later, and additionally electrically insulating the Peltier module leads from the plates, preventing short circuiting. After the thin layer, individual spacers can be adhered on a per plate/module basis around the perimeter of the components, heat sinks, and adhesives. These will provide clearance that prevents some mechanical stresses that would weaken the adhesives over time.

Flexible vinyl tubing can be used to fluidly couple the heat sinks in series. The leads of the Peltier modules should also be electrically connected at this time. Using 12706 Peltier modules and a 12V power supply, groups of four modules in series, the groups being parallelly connected, is good for electrical efficiency, as well as comfortable but powerful cooling.

At this point a module-elastic continuous body has been formed with an inlet and outlet vinyl tube and one positive and one negative lead. If the entire device is flipped over, it will reveal the plates with the exposed layer of thin foam. A membrane can now be shaped and cut out to bind to the thin layer while leaving the plates exposed. Marine-grade (waterproof) fabric works well for the membrane and doubles as a non-absorbing layer that protects components from moisture and debris.

A reservoir with a pump allows for longer duration of use. The reservoir can be made of anything, but, assuming a portable and standalone design is desired, 2 gallon jugs with a handle help with portability while still providing enough thermal mass for hours of use. The pump should be designed to operate at the same voltage as the Peltier module groupings. In this case, that's 12V, and the pump should be electrically connected in parallel with the module groupings. The inlet vinyl tube should be extended to the outlet of the pump, which is submerged in the reservoir, while the outlet tube should be extended into the reservoir.

A power source can now be electrically connected to the pump and module groupings with an on-off switch. When turned on, water should flow from the pump, through the vinyl tubing and all of the heat sinks, and then back into the reservoir.

If the Peltier modules weren't tested beforehand, their polarity may need to reverse in order for the plates to get cold. As long as they are all adhered to the plates in the same orientation beforehand, this is trivial. The Peltier modules can have ink labels on one side, that side being adhered to the plates, so that when the positive leads and negative leads are connected (red to red, black to black) with the power source the plates will become cold.

Each of the components of the flexible thermoelectric device described herein may be manufactured and/or assembled in accordance with the conventional knowledge and level of a person having skill in the art.

While various details, features, combinations are described in the illustrated embodiments, one having skill in the art will appreciate a myriad of possible alternative combinations and arrangements of the features disclosed herein. As such, the descriptions are intended to be enabling only, and non-limiting. Instead, the spirit and scope of the invention is set forth in the appended claims.

First Illustrated Embodiment

FIG. 1A shows a perspective view of one of a plurality of modules (110) in accordance with a first illustrated embodiment. Each of the plurality of modules comprises a thermoelectric component (130) coupled to a thermally conductive plate (120) and further coupled to a heat sink (140). The thermoelectric component comprises a component top side (131) and a component bottom side (132) opposite the component top side. The component bottom side is coupled to a plate top surface (121) of the thermally conductive plate. The component top side is coupled to a heat sink bottom surface of the heat sink wherein the heat sink bottom surface is opposite a heat sink top surface (141). Coupling between the thermoelectric component and the thermally conductive plate and/or heat sink can be achieved by an adhesive (134) as can be appreciated by one having skill in the art. The thermally conductive plate further comprises a plate bottom surface (122) opposite the plate top surface. The plate bottom surface is configured to contact a user, either directly or indirectly. The thermoelectric component further comprises electrodes (135) configured to receive power from a power source for powering to the thermoelectric component.

The heat sink (140) further comprises a first aperture (144), a second aperture (145), and a hollow cavity (not shown) disposed within the heat sink and fluidly coupled to each of the first and second apertures. In some embodiments, the heat sink may comprise more than two apertures. The first and second apertures are each configured to fluidly couple with a heat sink of another module or an external reservoir.

Figure 1B:
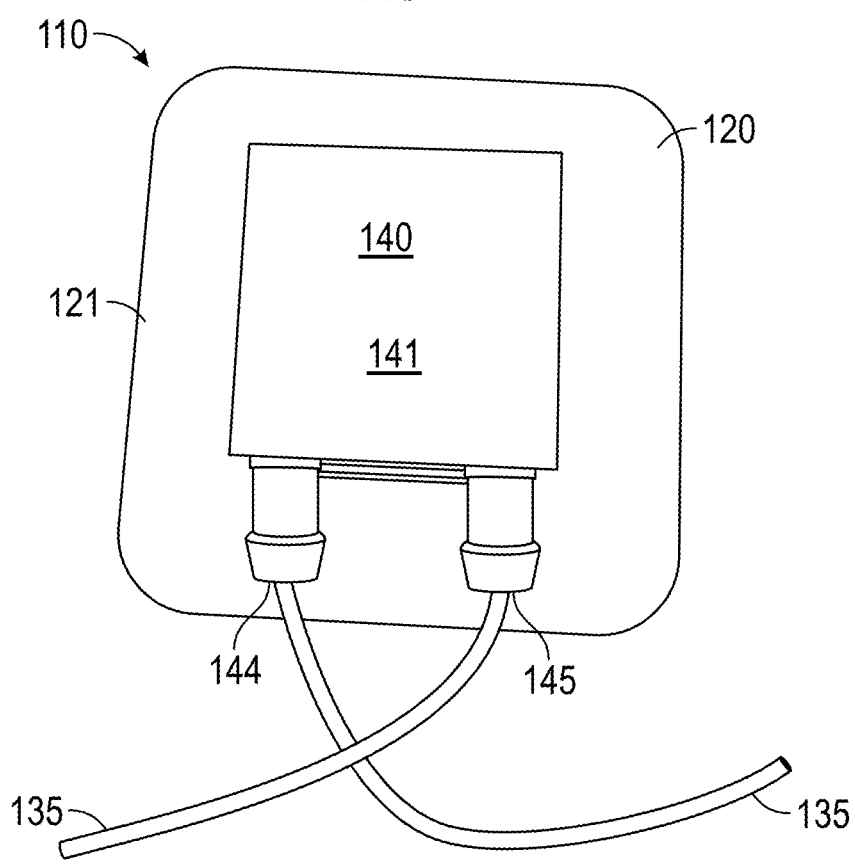
FIG. 1B shows a top view of the one of the plurality of modules in accordance with a first illustrated embodiment.

FIG. 1B shows a top view of the one of the plurality of modules (110) in accordance with a first illustrated embodiment. The module comprises a thermally conductive plate (120), a heat sink (140), and a thermoelectric component (not shown) disposed therebetween. The thermally conductive plate couples to the thermoelectric component at a plate top surface (121). The heat sink comprises a heat sink top surface (141) which is free from any coupling. The heat sink comprises a first aperture (144) and a second aperture (145) disposed on a common side of the heat sink. The first aperture or the second aperture are configured to fluidly couple with at least one heat sink of another module. Electrodes (135) of the thermoelectric component extend outward from the thermoelectric component and beneath each of the first and second apertures.

Figure 2:
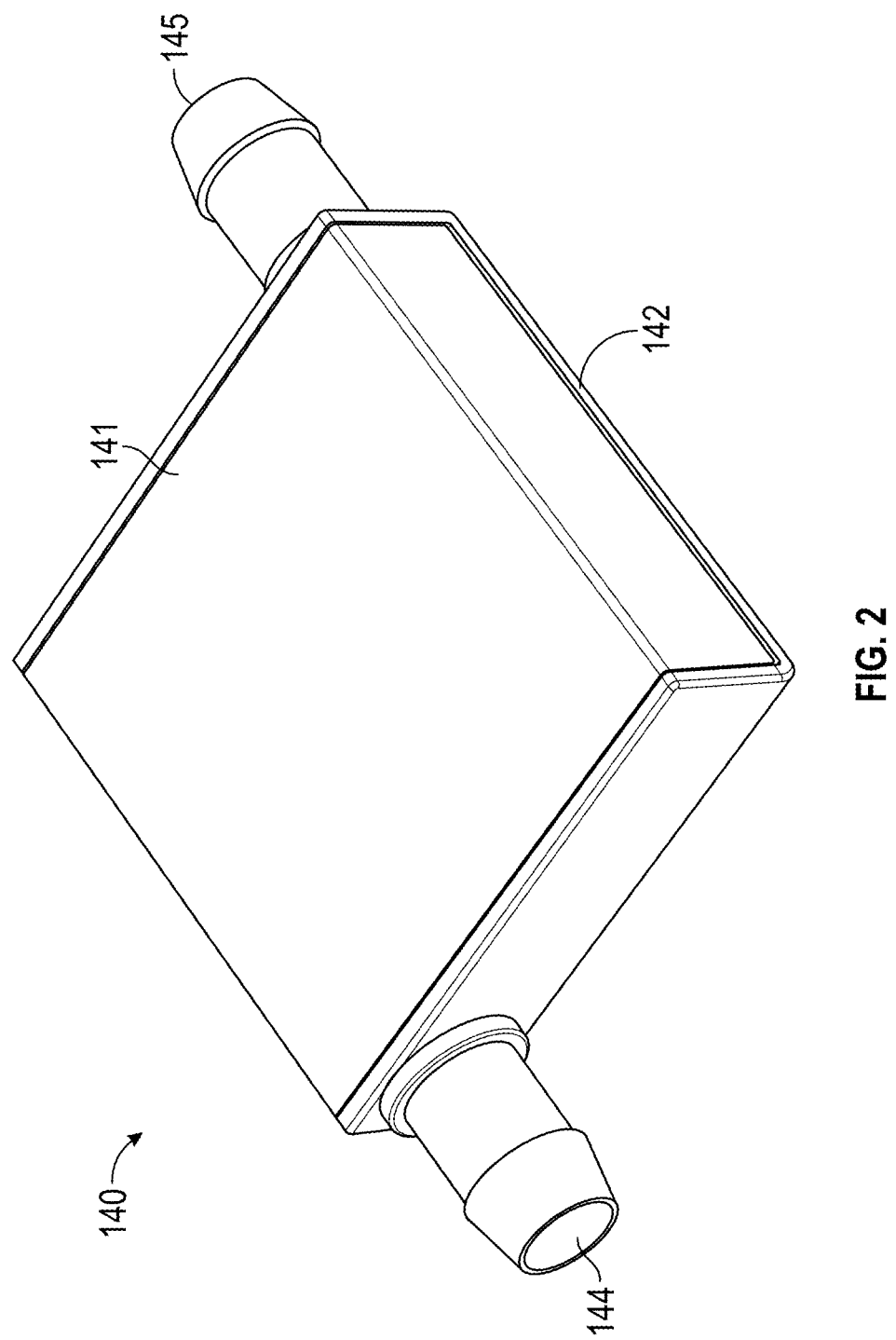
FIG. 2 shows a perspective view of an alternative heat sink.

FIG. 2 shows a perspective view of an alternative heat sink (140). The heat sink comprises a heat sink top surface (141) and a heat sink bottom surface (142) opposite the heat sink top surface. The heat sink further comprises a first aperture (144) and a second aperture (145) disposed on opposite sides of the heat sink. In other embodiments, the first and second apertures may be disposed on adjacent sides of the heat sink.

Figure 3:
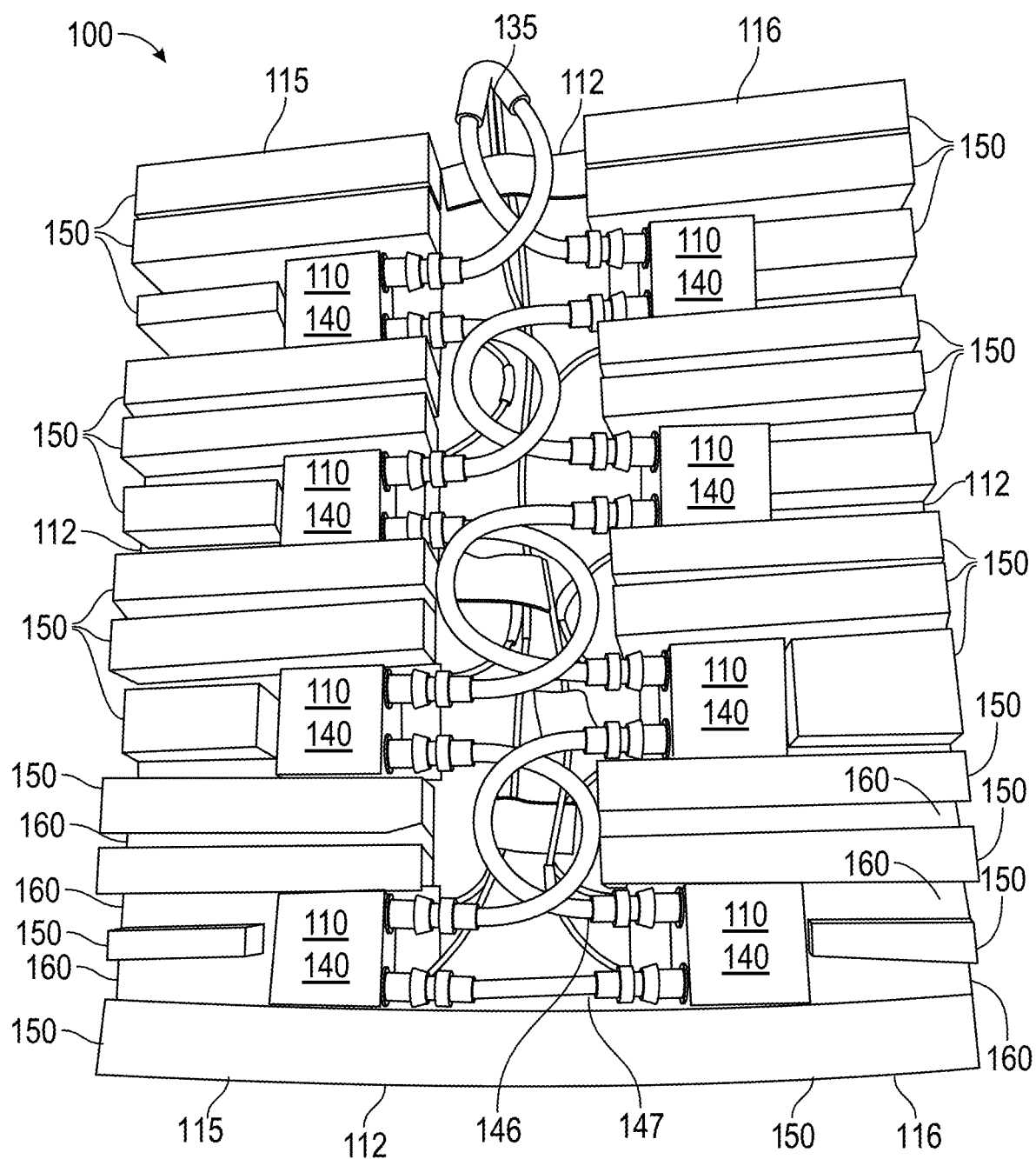
FIG. 3 shows a top view of a flexible thermoelectric device in accordance with the first illustrated embodiment.

FIG. 3 shows a top view of a flexible thermoelectric device (100) in accordance with the first illustrated embodiment. The flexible thermoelectric device comprises a plurality of modules (110) coupled to an elastic material (160). Coupled to the elastic material and disposed around the plurality of modules is a plurality of spacers (150). Gaps between each of the plurality of spacers expose the elastic material and allow the flexible thermoelectric device to bend. A middle section of the flexible thermoelectric device comprises a plurality of first fluid tubes (146) and second fluid tubes (147) for each of the plurality of modules. The first and second fluid tubes are fluidly coupled to heat sinks (140) of the plurality of modules. The middle section further comprises electrodes (135) for powering the plurality of modules.

The plurality of spacers (150) is configured to protect each of the plurality of modules (110) by preventing each heat sink (140) to experience a downward force, which can subsequently create a torsional force between thermoelectric components and thermally conductive plates of each of the plurality of module, thereby causing breakage of the modules. The plurality of spacers is positioned such that at least one spacer is disposed between two neighboring modules. "Neighboring modules" is defined as adjacent modules on either a first side (115) or second side (116) wherein the middle section is disposed between the first side and the second side. Furthermore, the plurality of spacers is positioned such that at least one spacer is disposed between each of the plurality of modules and an outer device periphery (112). Each of the heat sinks is fluidly coupled to at least one other heat sink.

Figure 4:
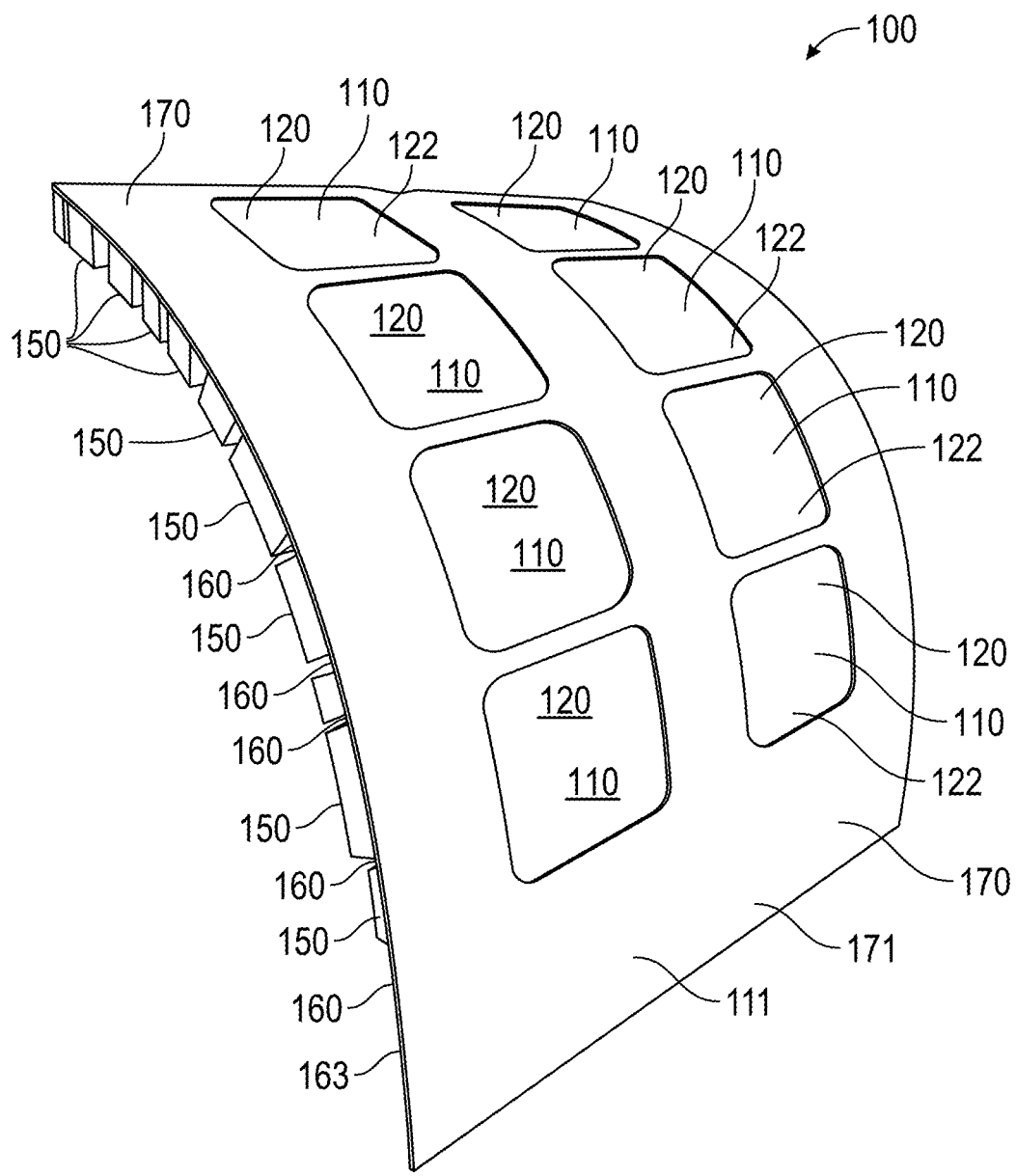
FIG. 4 shows a bottom perspective view of the flexible thermoelectric device in accordance with the first illustrated embodiment.

FIG. 4 shows a bottom perspective view of the flexible thermoelectric device (100) in accordance with the first illustrated embodiment. The flexible thermoelectric device comprises a plurality of modules (110) coupled to an elastic material (160). The elastic material comprises a plurality of spacers (150) configured to protect the plurality of modules while allowing the thermoelectric device to bend and flex and may be configured to conform to a curved surface. The plurality of modules each include a thermally conductive plate (120) having a plate bottom surface (122). As shown, the device further comprises a membrane (170) coupled to the elastic material. The membrane comprises a membrane bottom surface (171) wherein the membrane bottom surface and the plate bottom surface form a bottom device plane (111) such that the membrane bottom surface and the plate bottom surface form a smooth surface. In other embodiments, the membrane and the elastic material are integrated with each other such that the membrane is the elastic material.

Figure 5:
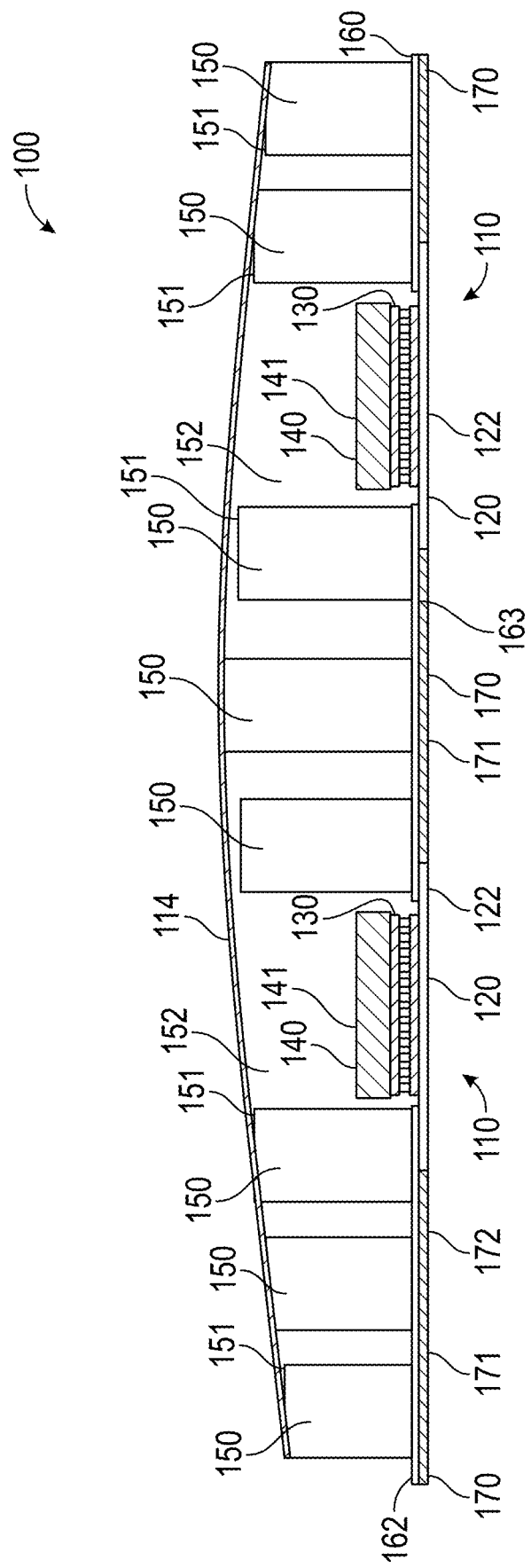
FIG. 5 shows a side cross-section view of the flexible thermoelectric device in accordance with the first illustrated embodiment.

FIG. 5 shows a side cross-section view of the flexible thermoelectric device (100) in accordance with the first illustrated embodiment. The flexible thermoelectric device includes a plurality of modules (110) each comprising a thermally conductive plate (120) coupled to a thermoelectric component (130). The thermoelectric component is coupled to a heat sink (140). Each of the plurality of modules is coupled to an elastic material (160) at the thermally conductive plate. A membrane (170) is coupled to the elastic material at an elastic bottom surface (163). The membrane includes a membrane bottom surface (171) opposite coupling of the membrane with the elastic bottom surface. As shown, the membrane is also a non-absorbing layer (172) configured to prevent moisture from passing through the elastic material and damaging electronics and other components of the device. In other embodiments, the non-absorbing layer may be a separate layer coupled to the membrane bottom surface. Coupled to an elastic top surface (162) opposite the elastic bottom surface includes a plurality of spacers (150) comprising varying heights. In other embodiments the plurality of spacers comprises a common height.

Each of the plurality of spacers (150) comprises a spacer top surface (151). The plurality of spacers is configured to minimize or eliminate force applied to a heat sink top surface (141) and subsequently other portions of the plurality of modules (110). This minimization or elimination is achieved by the spacer top surface and the heat sink top surface forming a clearance (152) such that the spacer top surface of each of the plurality of spacers is disposed further from the thermally conductive plates (120) than each of the heat sink top surfaces. An optional back cover (114) is coupled to some of the plurality of spacers at the spacer top surface. During use of the flexible thermoelectric device (100), as pressure is applied to a plate bottom surface (122) of the thermally conductive plates in addition to the membrane, clearance from the plurality of spacers prevent the back cover from pressing against the plurality of modules, thereby increase durability of the device.

Figure 6:
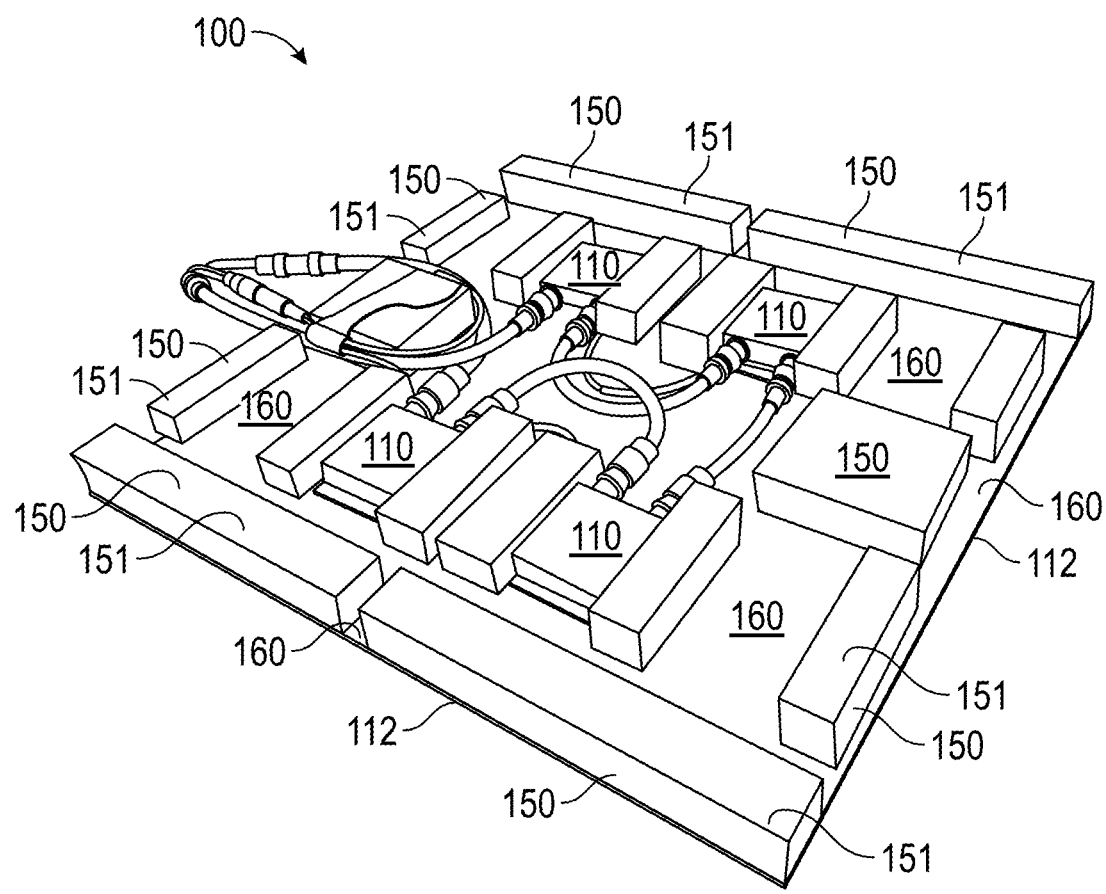
FIG. 6 shows a perspective view of an alternate flexible thermoelectric device in accordance with the first illustrated embodiment.

FIG. 6 shows a perspective view of an alternate flexible thermoelectric device (100) in accordance with the first illustrated embodiment. The flexible thermoelectric device comprises an elastic material (160) forming a layer and having a device outer periphery (112). Coupled to the elastic material is a plurality of modules (110) and a plurality of spacers (150). The plurality of spacers is disposed at sides of each of the plurality of modules and is further disposed along the outer device periphery. Each of the plurality of modules has at least one spacer disposed between the module and a nearby edge of the outer device periphery. Each of the plurality of spacers comprises a spacer top surface (151) extending higher than each of the plurality of modules to aid in durability.

Second Illustrated Embodiment

Figure 7:
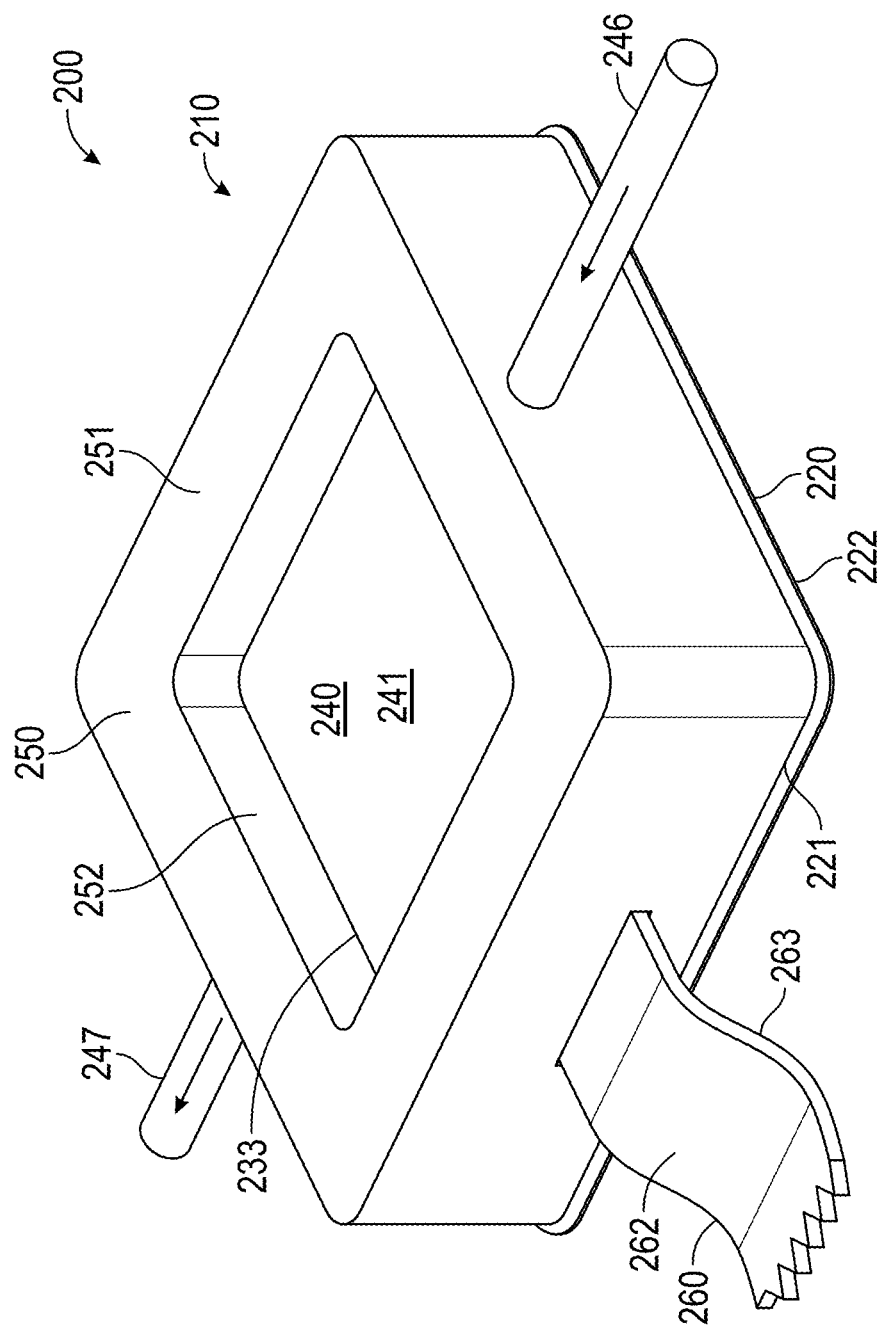
FIG. 7 shows a perspective view of a flexible thermoelectric device in accordance with a second illustrated embodiment.

FIG. 7 shows a perspective view of a flexible thermoelectric device (200) in accordance with a second illustrated embodiment. As shown, the thermoelectric device comprises one of a plurality of modules (210). Each of the plurality of modules comprises a thermally conductive plate (220), a heat sink (240), and a thermoelectric component (not shown) disposed therebetween. A plurality of spacers (250) surrounds both the thermoelectric component and the heat sink and couples to each adjacent spacer which causes the plurality of spacers surrounding the thermoelectric component and heat sink to form a single cohesive perimeter (233). In other embodiments, the plurality of spacers does not form a single cohesive perimeter and instead comprise individual spacers. The plurality of spacers includes a spacer top surface (251) which extends higher than a heat sink top surface (241) to form a clearance (252).

The flexible thermoelectric device further comprises a first fluid tube (246) and a second fluid tube (247) each fluidly coupled to the heat sink and extending through a section of the plurality of spacers (250). An elastic material (260) having an elastic top surface (262) and an elastic bottom surface (263) also extends through the plurality of spacers. The first and second fluid tubes may also comprise an elastic material to aid in the device's flexibility. In some embodiments, each of the device's elastic material are fluid tubes. The thermally conductive plate includes a plate top surface (221) and a plate bottom surface (222) opposite the plate top surface. The plurality of spacers is coupled to the plate top surface and the plate bottom surface is configured to face a user.

Figure 8:
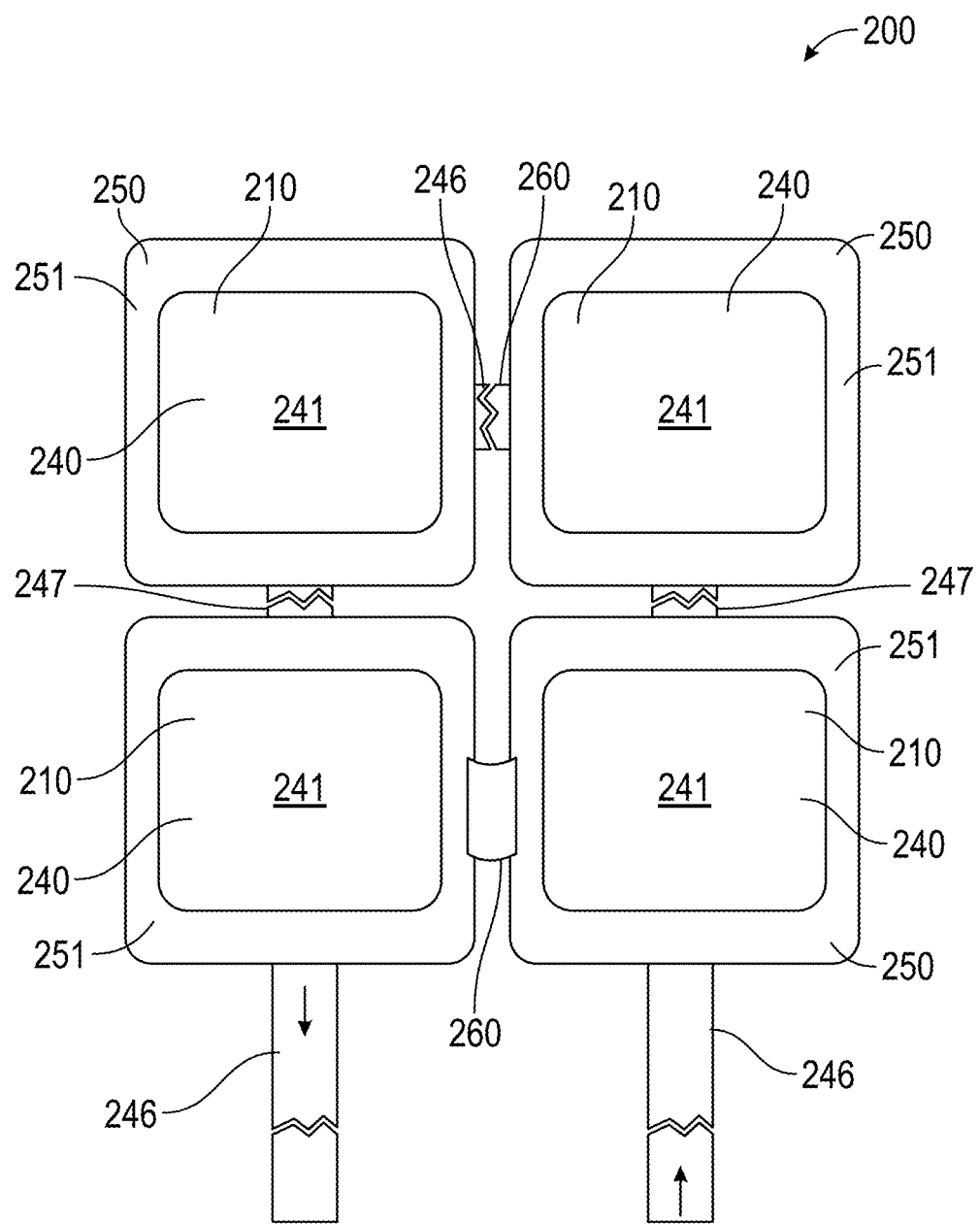
FIG. 8 shows a top view of the flexible thermoelectric device in accordance with the second illustrated embodiment.
Figure 9:
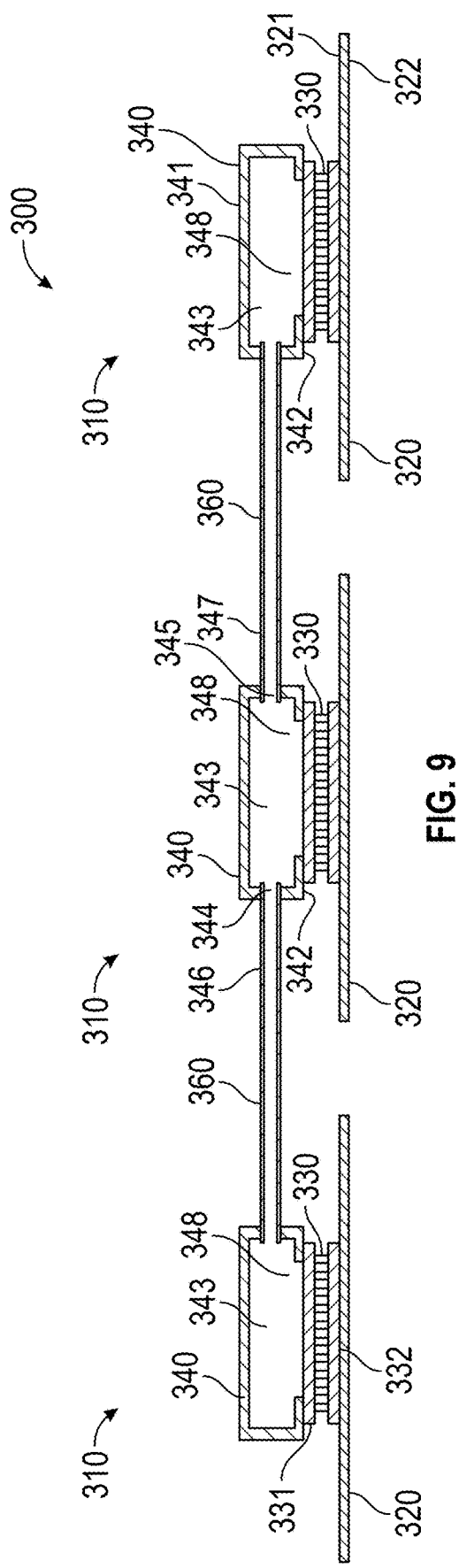
FIG. 9 shows a side cross-section view of a flexible thermoelectric device in accordance with a third illustrated embodiment.

FIG. 8 shows a top view of the flexible thermoelectric device (200) in accordance with the second illustrated embodiment. The flexible thermoelectric device comprises a plurality of modules (210) each surrounded by a plurality of spacers (250). Each of the plurality of modules comprises a thermally conductive plate, a thermoelectric component, and a heat sink (240). A heat sink top surface (241) of the heat sink can be seen from above. A heat sink bottom surface (not shown) is disposed opposite the heat sink top surface. Each of the plurality of modules is coupled to at least one other module by an elastic material (260) and/or fluid tube; either first (246) or second (247). It will be appreciated that first and second designations for fluid tubes are arbitrary and used merely to differentiate multiple fluid tubes that are fluidly coupled to a heat sink. Some or all the fluid tubes may also comprise the elastic material to be used instead of or in addition to the elastic material strip shown Third Illustrated Embodiment FIG. 9 shows a side cross-section view of a flexible thermoelectric device (300) in accordance with a third illustrated embodiment. The flexible thermoelectric device comprises a plurality of modules (310) wherein each of the plurality of modules comprises a thermoelectric component (330) coupled to both a heat sink (340) and a thermally conductive plate (320). Specifically, the thermoelectric component has a component top side (331) and a component bottom side (332) opposite the component top side. The heat sink comprises a heat sink top surface (341) and a heat sink bottom surface (342) opposite the heat sink top surface. The thermally conductive plate comprises a plate top surface (321) and a plate bottom surface (322) opposite the plate top surface. The plurality of modules is constructed such that the plate top surface is coupled to the component bottom side and the component top side is coupled to the heat sink bottom surface. Both the plate bottom surface and the heat sink top surface are free from coupling.

Each of the plurality of modules (310) is fluidly coupled with at least one other module via fluid tubes coupled to each heat sink (340). As shown, a first fluid tube (346) and a second fluid tube (347) are both fluidly coupled to the heat sink of the center module. The first fluid tube is fluidly coupled with the heat sink of one module while the second fluid tube is fluidly coupled with the heat sink of another module. Each heat sink comprises a first aperture (344) and a second aperture (345) which are configured to receive a fluid tube.

The heat sink (340) of each of the plurality of module (310) further comprises a hollow cavity (343) for receiving and sending fluid through the first and second apertures through the fluid tubes to a neighboring module. The heat sink includes an opening (348) at the heat sink bottom surface (342). The opening, which is disposed between the hollow cavity and the component top side (331) of the thermoelectric component (330), allows fluid to directly contact the thermoelectric component for direct cooling. The opening may comprise a single hole or may comprise a plurality of holes. In other embodiments, the heat sink does not comprise an opening between the hollow cavity and the thermoelectric component such that fluid traveling through the heat sink is configured to indirectly cool the thermoelectric element.

The flexible thermoelectric device (300) further comprises an elastic material (360) to provide the device a flexibility for easy conformity to various surfaces, such as a chair. As shown, the fluid tubes, namely the first fluid tube (346) and the second fluid tube (347) are also the elastic material of the device.

In an embodiment where the flexible thermoelectric device (300) is configured to cool a user, the plate bottom surface (322) is configured to contact the user. The component bottom side (332) of the thermoelectric component (330) is cooled while the thermoelectric component receives electricity from a power source. The cooled component bottom side cools the thermally conductive plate (320), and subsequently the plate bottom surface (322), for providing a cooled surface to the user. While the component bottom side is cooled by the thermoelectric component, the component top side (331) is alternatively heated up. Fluid traveling through fluid tubes and each of the heat sinks (340) directly removes heat from the component top side.

Fourth Illustrated Embodiment

Figure 10:
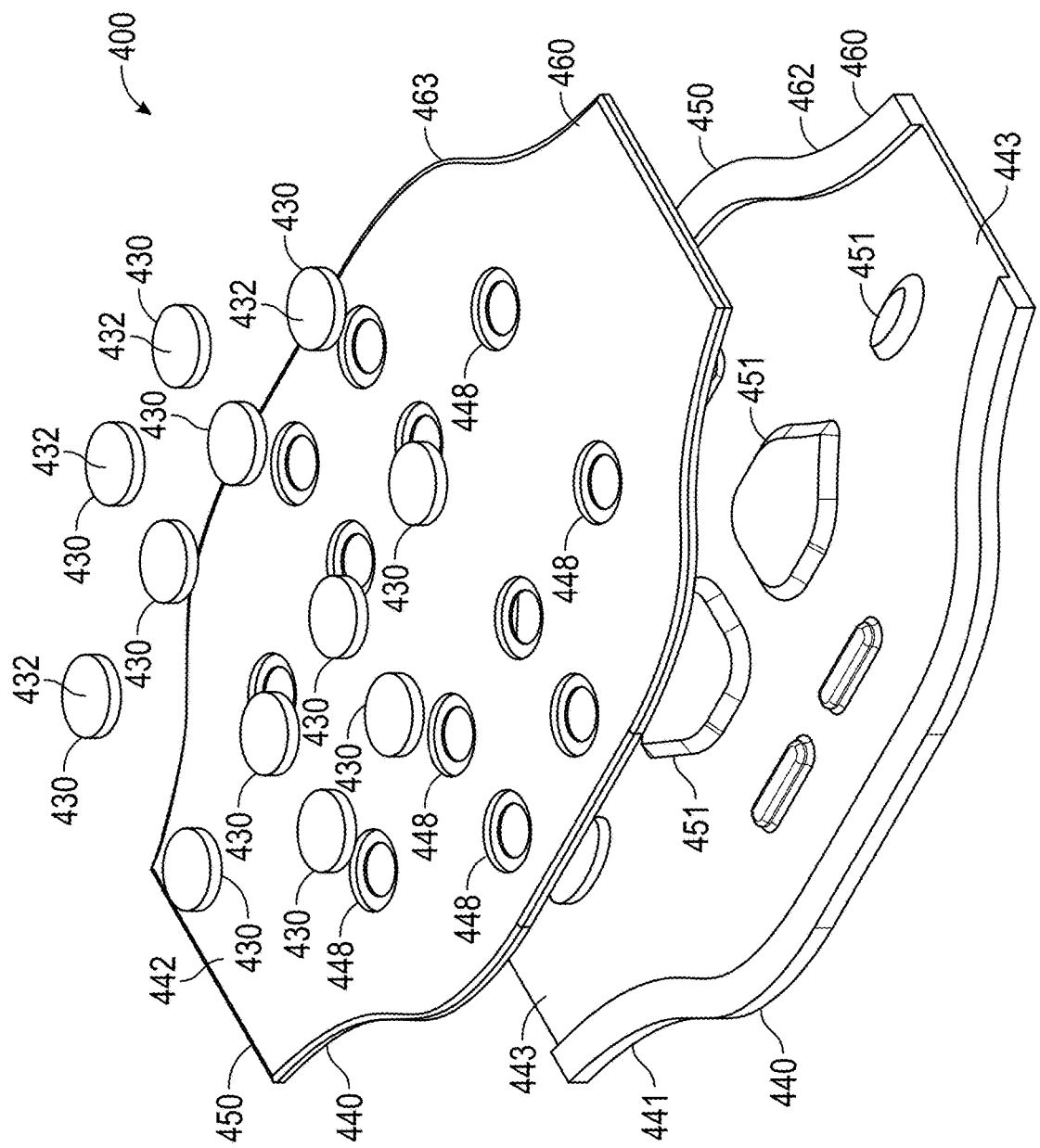
FIG. 10 shows an exploded perspective view of a flexible thermoelectric device in accordance with a fourth illustrated embodiment.

FIG. 10 shows an exploded perspective view of a flexible thermoelectric device (400) in accordance with a fourth illustrated embodiment. An elastic mesh is shown in two layers of elastic material (460), each of which has an elastic top surface (462) opposite an elastic bottom surface (463). In practice, these layers could be formed in one piece or separately with the elastic bottom surface of one layer coupled to the elastic top surface of another layer in order to create a fluid-tight coupling and a hollow cavity (443) disposed therebetween. This design comprises a heat sink (440) having a heat sink top surface (441) and a heat sink bottom surface (442) and could be characterized as a bladder (450).

The elastic bottom surface (463) of the bladder (450) has a plurality of openings (448) that are fluidly coupled with the hollow cavity (443). An equal number of thermoelectric components (430), each having a component bottom side (432) opposite a component top side, are disposed in the openings with a fluid-tight coupling between each of the component top surfaces and the elastic bottom surface. Inner surfaces of the bladder may have raised surfaces (451) that strategically reduce flexibility of the bladder, thereby protecting components and couplings from unwanted mechanical stress. As shown, the flexible thermoelectric device (400) is a thin and lightweight design that can enhance portability and promote passive fluid cycling.

Figure 11:
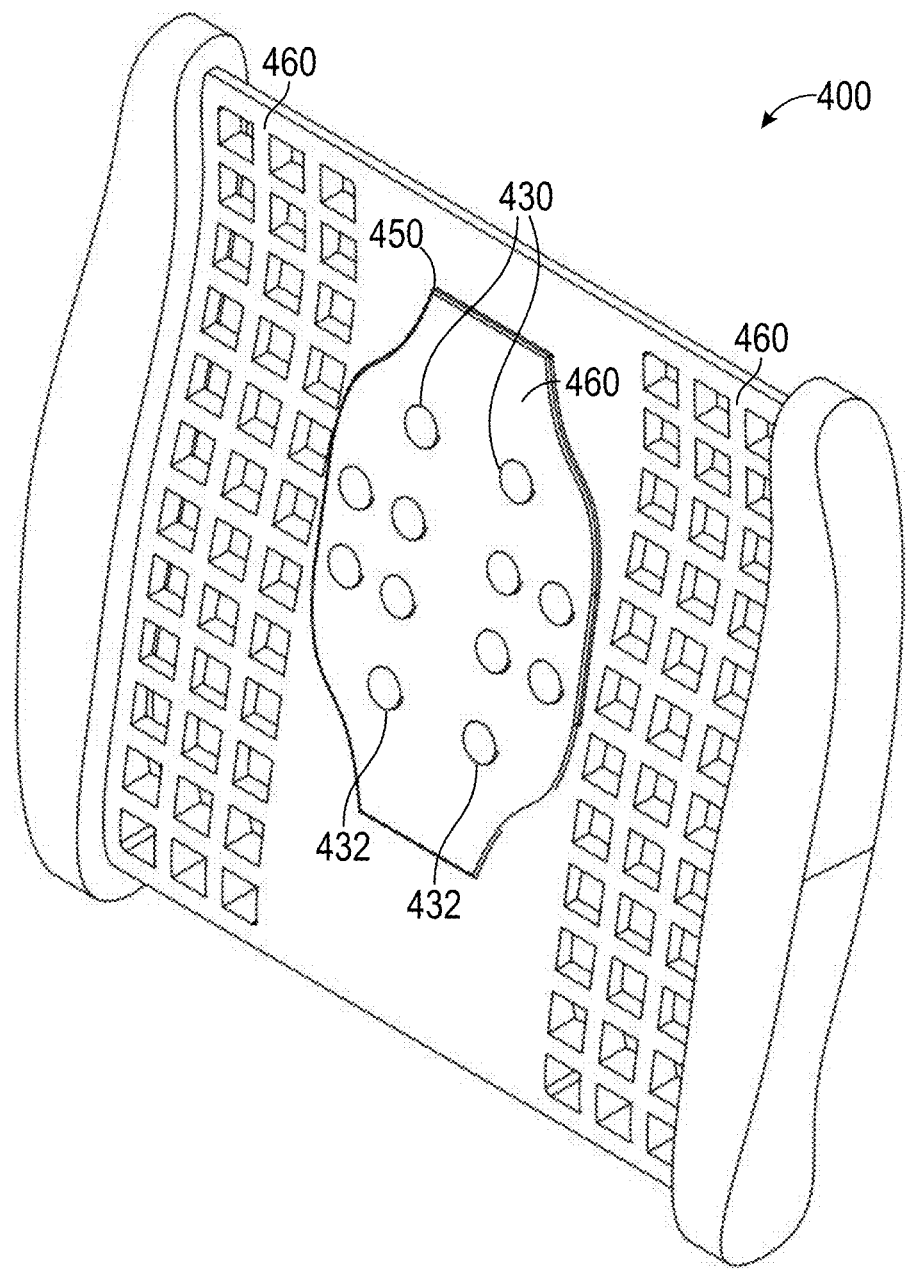
FIG. 11 shows a perspective view of a flexible thermoelectric device in accordance with the fourth illustrated embodiment.

FIG. 11 shows a perspective view of a flexible thermoelectric device (400) in accordance with a fourth illustrated embodiment. The bladder (450) in FIG. 10 is further integrated into a suspended elastic mesh made of elastic material (460), configured to be the backrest of a piece of furniture. The bladder is installed such that the component bottom sides (432) of the thermoelectric components (430) are facing the user of the backrest. This combined bladder and suspended mesh design helps prevent unwanted mechanical stresses on the components from the top (rear of furniture from the user's perspective).

Fifth Illustrated Embodiment

Figure 12:
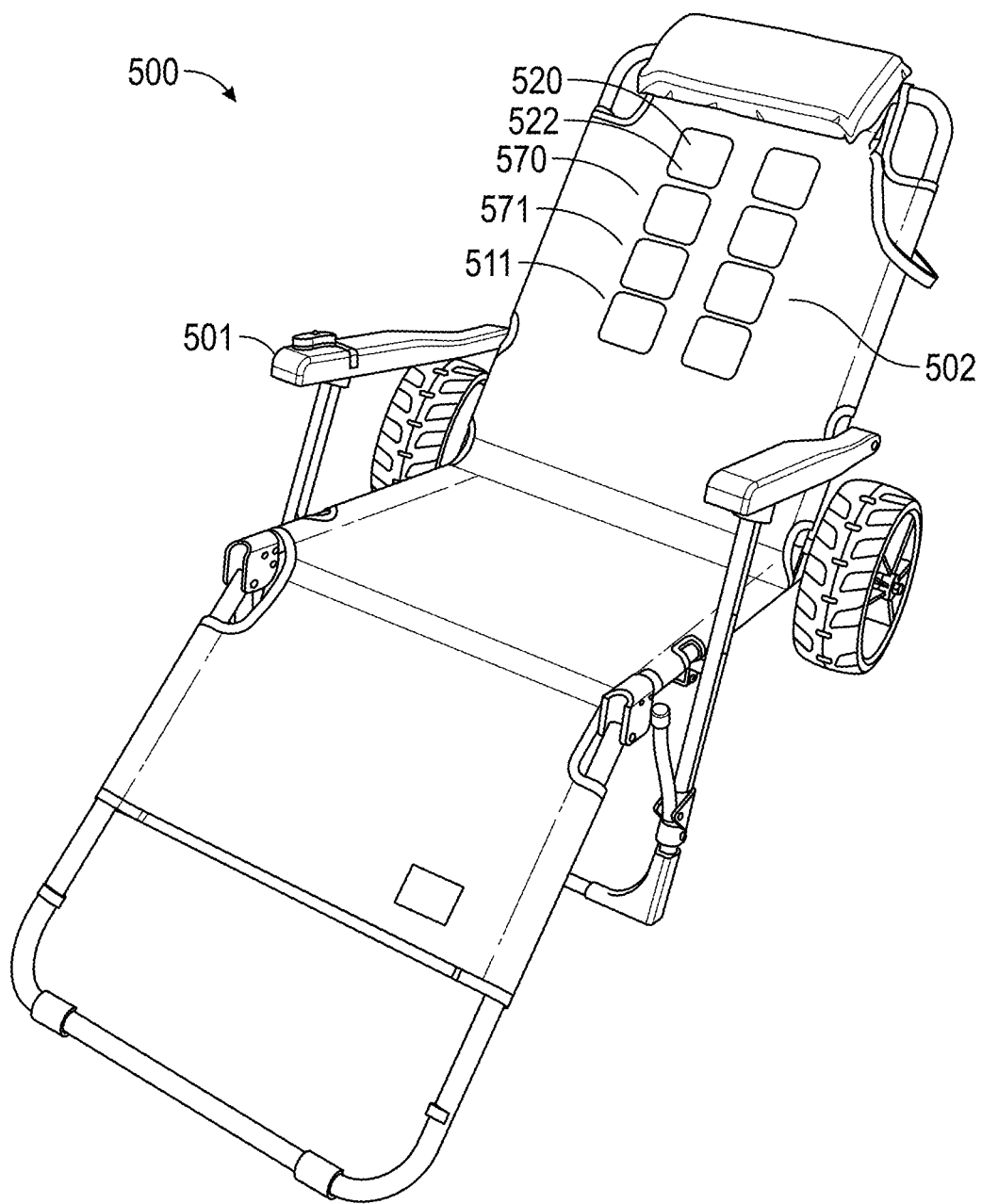
FIG. 12 shows a perspective view of a flexible thermoelectric device in accordance with a fifth illustrated embodiment.

FIG. 12 shows a perspective view of a flexible thermoelectric device (500) in accordance with a fifth illustrated embodiment. The device is incorporated into a backrest of a piece of furniture (501). The furniture surface (502) is composed in part by a membrane (570). The plates (520) and membrane are positioned such that the bottom device plane (511), plate bottom surfaces (522), and membrane bottom surface (571) form a smooth surface.

Sixth Illustrated Embodiment

Figure 13B:
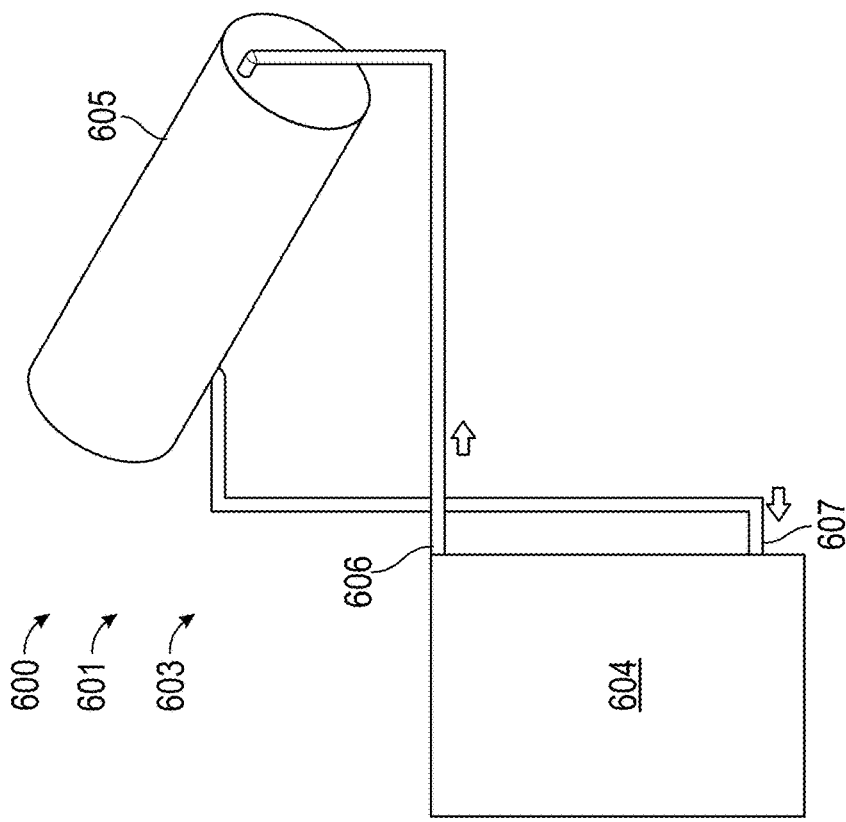
FIG. 13A-B show a block diagram of various fluid cycling methods in accordance with a sixth illustrated embodiment.
Figure 13A:
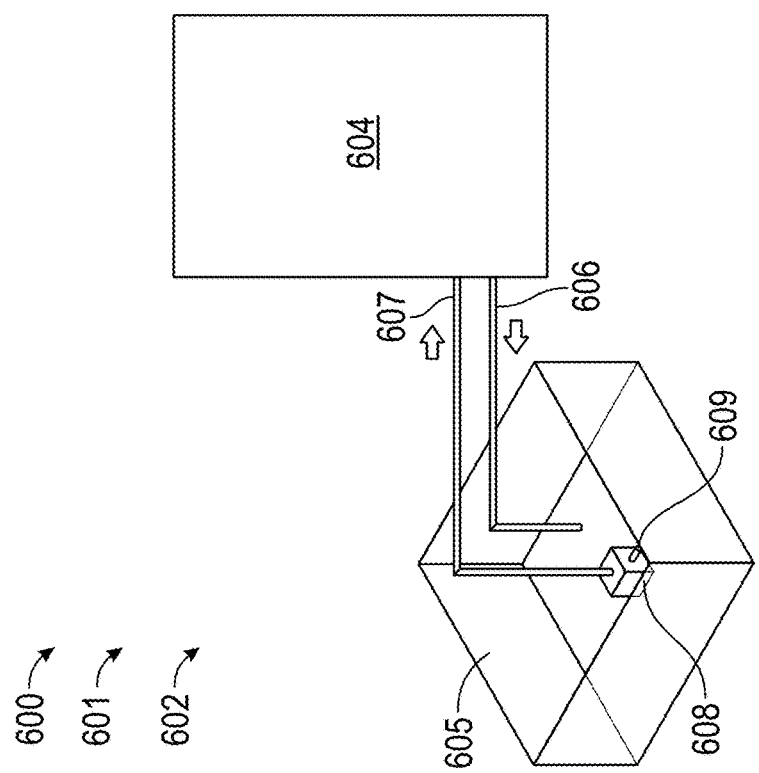

FIG. 13A-B show a block diagram of various fluid cycling methods (600) in accordance with a sixth illustrated embodiment. Each fluid cycling method comprises one flow mechanism (601). For simplicity, a module-elastic continuous body (604) is abstracted and it is assumed that fluidly coupled components therein are a sealed system except for a single inlet (607) and a single outlet (606). Two flow mechanisms, namely a pump-reservoir mechanism (602) and a thermosiphon mechanism (603), are illustrated for exemplary purposes among a myriad of other flow mechanisms. In both flow mechanisms, the inlet and outlet are coupled with an external reservoir (605). Both flow mechanisms are shown as both being used with the module-elastic continuous body for illustrative purposes. One having skill in the art will appreciate that a single flow mechanism, such as the pump-reservoir mechanism, the thermosiphon mechanism or an alternative flow mechanism, would be implemented for each individual module-elastic continuous body.

FIG. 13A shows the pump-reservoir mechanism (602), wherein the reservoir (605) comprises an electromechanical fluid pump (608) electrically connected to a power source (609). Fluid is pushed through the inlet (607), heat sink(s) within the module-elastic continuous body (604), the outlet (606), and then back into the reservoir. Since the performance of thermoelectric components varies widely based on several factors, this mechanism allows for more predictable operation.

FIG. 13B shows the thermosiphon mechanism (603), wherein the entire fluidly coupled system is sealed. Convection currents move warmer fluid from the module-elastic continuous body (604) through the outlet (606) and into the top of the reservoir (605), pushing colder fluid from the bottom of the reservoir through the inlet (607). The fluid in contact with heat sinks within the module-elastic continuous body is thereby passively replenished with the coldest available fluid in the system. The thermosiphon mechanism removes pump noise and the risk of long-term wear and tear of moving parts, creating an additional advantage over air conditioning.

FEATURE LIST flexible thermoelectric device (100; 200; 300; 400; 500)
plurality of modules (110; 210; 310)
bottom device plane (111; 511)
device outer periphery (112)
back cover (114)
first side (115)
second side (116)
thermally conductive plate (120; 220; 320; 520)
plate top surface (121; 221; 321)
plate bottom surface (122; 222; 322; 522)
thermoelectric component (130; 330; 430)
component top side (131; 331)
component bottom side (132; 332; 432)
perimeter (233)
adhesive (134)
electrodes (135)
heat sink (140; 240; 340; 440)
heat sink top surface (141; 241; 341; 441)
heat sink bottom surface (142; 342; 442)
hollow cavity (143; 343; 443)
first aperture (144; 344)
second aperture (145; 345)
first fluid tube (146; 246; 346)
second fluid tube (147; 247; 347)
plurality of spacers (150; 250)
spacer top surface (151; 251)
clearance (152; 252)
elastic material (160; 260; 360; 460)
elastic top surface (162; 262; 462)
elastic bottom surface (163; 263; 463)
membrane (170; 570)
membrane bottom surface (171; 571)
non-absorbing layer (172)
opening (348; 448)
bladder (450)
raised surfaces (451)
furniture (501)
furniture surface (502)
fluid cycling method (600)
flow mechanism (601)
pump-reservoir mechanism (602)
thermosiphon mechanism (603)
module-elastic continuous body (604)
reservoir (605)
outlet (606)
inlet (607)
pump (608)
power source (609)

What is claimed is:

1. A flexible thermoelectric device, comprising:
   a plurality of modules, each of the plurality of modules comprising:
   a thermally conductive plate having a plate top surface and a plate bottom surface opposite the plate top surface,
   a thermoelectric component having a component top side and a component bottom side opposite the component top side, wherein the component bottom side is coupled to the plate top surface, and
   a heat sink having a heat sink top surface, a heat sink bottom surface opposite the heat sink top surface, wherein the heat sink bottom surface is coupled to the component top surface;
   a plurality of spacers wherein each of the plurality of spacers comprises a spacer top surface that extends vertically above the heat sink top surface of at least one of the plurality of modules, thereby forming a clearance between the spacer top surface and the heat sink top surface of the corresponding module, wherein the plurality of spacers are disjointed from each other;
   an elastic material coupled to two or more of the thermally conductive plates and one or more of the plurality of spacers thereby forming a continuous body; and
   a power source electrically coupled to the plurality of modules;
   wherein the heat sink of each of the plurality of modules is configured to be fluidly coupled to at least one other heat sink.

2. The flexible thermoelectric device of claim 1, further comprising a device outer periphery surrounding each of the plurality of modules wherein at least one of the plurality of spacers is disposed between each of the plurality of modules and the device outer periphery.

3. The flexible thermoelectric device of claim 1, wherein at least one of the plurality of spacers is disposed between neighboring modules.

4. The flexible thermoelectric device of claim 1, the heat sink further comprising:
   a first aperture;
   a second aperture;
   a first fluid tube coupled to the first aperture; and
   a second fluid tube coupled to the second aperture.

5. The flexible thermoelectric device of claim 4, wherein the first and second fluid tubes and the elastic material are independent and distinct.

6. The flexible thermoelectric device of claim 4, wherein the first fluid tube and the second fluid tube each extend through at least one of the plurality of spacers.

7. The flexible thermoelectric device of claim 1, wherein the plurality of modules is fluidly coupled in series, parallel, or a combination thereof.

8. The flexible thermoelectric device of claim 1, wherein the plate top surface extends beyond the component bottom surface.

9. The flexible thermoelectric device of claim 1, wherein the elastic material surrounds an entire perimeter of the thermoelectric component.

10. The flexible thermoelectric device of claim 1, wherein each of the thermoelectric components is surrounded by at least one of the plurality of spacers.

11. The flexible thermoelectric device of claim 1, wherein each of the heat sinks is surrounded by at least one of the plurality of spacers.

12. The flexible thermoelectric device of claim 1, wherein the plate bottom surface of each of the plurality of modules forms a bottom device plane, the bottom device plane further comprising a membrane disposed on the bottom device plane, the membrane comprising a membrane bottom surface and a membrane top surface opposite the membrane bottom surface, wherein the membrane bottom surface and the plate bottom surface of each of the plurality of modules forms a smooth surface.

13. The flexible thermoelectric device of claim 12, wherein the elastic material comprises the membrane.

14. The flexible thermoelectric device of claim 12, wherein the membrane comprises a non-absorbing material.

15. The flexible thermoelectric device of claim 1, wherein the elastic material is coupled to the plate of each of the plurality of modules.

16. The flexible thermoelectric device of claim 1, each of the heat sinks further comprising a hollow cavity wherein each heat sink is configured to comprise an amount of fluid in the corresponding hollow cavity, and to heat or cool the corresponding thermoelectric component by conduction through the corresponding heat sink bottom surface.

17. The flexible thermoelectric device of claim 1, each of the heat sinks further comprising a hollow cavity wherein each heat sink is configured to comprise an amount of fluid in the corresponding hollow cavity, and to directly cool or heat the corresponding thermoelectric component via one or more openings in the corresponding heat sink bottom surface.

* * * * *